(12) United States Patent
Nishimura

(10) Patent No.: US 9,335,208 B2
(45) Date of Patent: May 10, 2016

(54) SCANNING ENDOSCOPE HAVING A RETURN LIGHT SELECTION UNIT

(71) Applicant: OLYMPUS CORPORATION, Tokyo (JP)

(72) Inventor: Junichi Nishimura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 168 days.

(21) Appl. No.: 14/296,828

(22) Filed: Jun. 5, 2014

(65) Prior Publication Data

US 2014/0284460 A1  Sep. 25, 2014

Related U.S. Application Data

(63) Continuation of application No. PCT/JP2012/082394, filed on Dec. 13, 2012.

(30) Foreign Application Priority Data

Dec. 20, 2011  (JP) .................................. 2011-278679
Aug. 24, 2012  (JP) .................................. 2012-184778

(51) Int. Cl.
*G01J 1/04*          (2006.01)
*A61B 1/00*          (2006.01)
(Continued)

(52) U.S. Cl.
CPC ............ *G01J 1/0403* (2013.01); *A61B 1/00096* (2013.01); *A61B 1/00172* (2013.01);
(Continued)

(58) Field of Classification Search
CPC ....... G01J 1/0425; G01J 3/0218; G01J 3/4412
USPC ............. 250/201.3, 239, 216, 214 R, 227.11, 250/227.29, 227.21, 462.1, 458.1; 359/367, 359/399–431, 589, 599, 618, 634, 483–502, 359/389, 385, 381; 356/318, 317, 417; 600/424–429, 478, 407, 178

See application file for complete search history.

(56) References Cited

U.S. PATENT DOCUMENTS 6,294,775 B1    9/2001  Seibel et al.
6,963,398 B2 *  11/2005  Sasaki ................ G01N 21/6458
                                                    250/462.1

(Continued)

FOREIGN PATENT DOCUMENTS

JP    02-214026 A    8/1990
JP    2004-065285 A  3/2004

(Continued)

OTHER PUBLICATIONS

Extended Supplementary European Search Report dated Aug. 7, 2015 from related European Application No. 12 86 0839.5.

(Continued)

*Primary Examiner* — Que T Le
(74) *Attorney, Agent, or Firm* — Scully, Scott, Murphy & Presser, P.C.

(57) ABSTRACT

There is provided a scanning endoscope including an optical scanning unit in which an angle at which illumination light is emitted from a leading edge of an insertion portion is changed to scan the emitted illumination light on an object, a plurality of light receiving portions which is circumferentially spaced apart at the leading edge of the insertion portion and receives return light returning from the object as a result of the optical scanning unit scanning the illumination light, a light detection unit that detects the intensity of the received return light, a return light selection unit that selects the return light whose intensity is equal to or smaller than a predetermined threshold, and a storage unit that stores the intensity of the return light selected by the return light selection unit in association with the position where the optical scanning unit scans the illumination light.

11 Claims, 5 Drawing Sheets

(51) Int. Cl.
*A61B 1/045* (2006.01)
*A61B 1/07* (2006.01)
*G01J 1/08* (2006.01)

(52) U.S. Cl.
CPC . *A61B1/045* (2013.01); *A61B 1/07* (2013.01); *G01J 1/0425* (2013.01); *G01J 1/08* (2013.01); *A61B 1/00009* (2013.01)

(56) References Cited

U.S. PATENT DOCUMENTS

| | | |
|---|---|---|
| 2002/0139920 A1 | 10/2002 | Seibel et al. |
| 2006/0195014 A1 | 8/2006 | Seibel et al. |
| 2008/0039693 A1 | 2/2008 | Karasawa |
| 2010/0123775 A1 | 5/2010 | Shibasaki |
| 2010/0137684 A1 | 6/2010 | Shibasaki et al. |

FOREIGN PATENT DOCUMENTS

| | | |
|---|---|---|
| JP | 2006-271871 A | 10/2006 |
| JP | 2008-531193 A | 8/2008 |
| JP | 2010-537771 A | 12/2010 |
| WO | WO 2006/093655 A2 | 9/2006 |
| WO | WO 2009/032016 A1 | 3/2009 |

OTHER PUBLICATIONS

International Search Report dated Feb. 26, 2013 issued in PCT/JP2012/082394.

Seibel, Eric J. et al., "Tethered Capsule Endoscopy, A Low-Cost and High-Performance Alternative Technology for the Screening of Esophageal Cancer and Barrett's Esophagus", IEEE Transactions on Biomedical Engineering (Mar. 2008), vol. 55, No. 3, pp. 1032-1042.

* cited by examiner

SCANNING ENDOSCOPE HAVING A RETURN LIGHT SELECTION UNIT

CROSS REFERENCE TO RELATED APPLICATIONS

This is a continuation of International Application PCT/JP2012/082394, with an international filing date of Dec. 13, 2012, which is hereby incorporated by reference herein in its entirety. This application claims the benefit of Japanese Patent Application No. 2011-278679 and 2012-184778, the contents of which are incorporated herein by reference.

TECHNICAL FIELD

The present invention relates to a scanning endoscope.

BACKGROUND ART

Until now, there has been known a scanning endoscope in which a leading edge of an optical fiber arranged at a leading edge of an insertion portion is rotated along a spiral locus to spirally scan illumination light emitted from the leading edge of the optical fiber on an object, the light returning from each scan position is received by a plurality of light receiving portions circumferentially spaced apart at the leading edge of the insertion portion, and light intensity associated with the scan position is stored, to thereby generate a two-dimensional image (refer to PTL 1, for example).

CITATION LIST

Patent Literature

{PTL 1}
U.S. Pat. No. 6,294,775

SUMMARY OF INVENTION

Solution to Problem

According to an aspect of the present invention, a scanning endoscope includes an optical scanning unit in which an angle at which illumination light is emitted from a leading edge of an insertion portion is changed to scan the emitted illumination light on an object, a plurality of light receiving portions which is circumferentially spaced apart at the leading edge of the insertion portion and receives return light returning from the object as a result of the optical scanning unit scanning the illumination light, a light detection unit that detects an intensity of the return light received by the light receiving portion, a return light selection unit that selects the return light whose intensity, which is detected by the light detection unit, is equal to or smaller than a predetermined threshold, and a storage unit that stores the intensity of the return light selected by the return light selection unit in association with a position where the optical scanning unit scans the illumination light.

DESCRIPTION OF EMBODIMENTS

A scanning endoscope 1 according to an embodiment of the present invention is described below with reference to the accompanied drawings.

Figure 1:
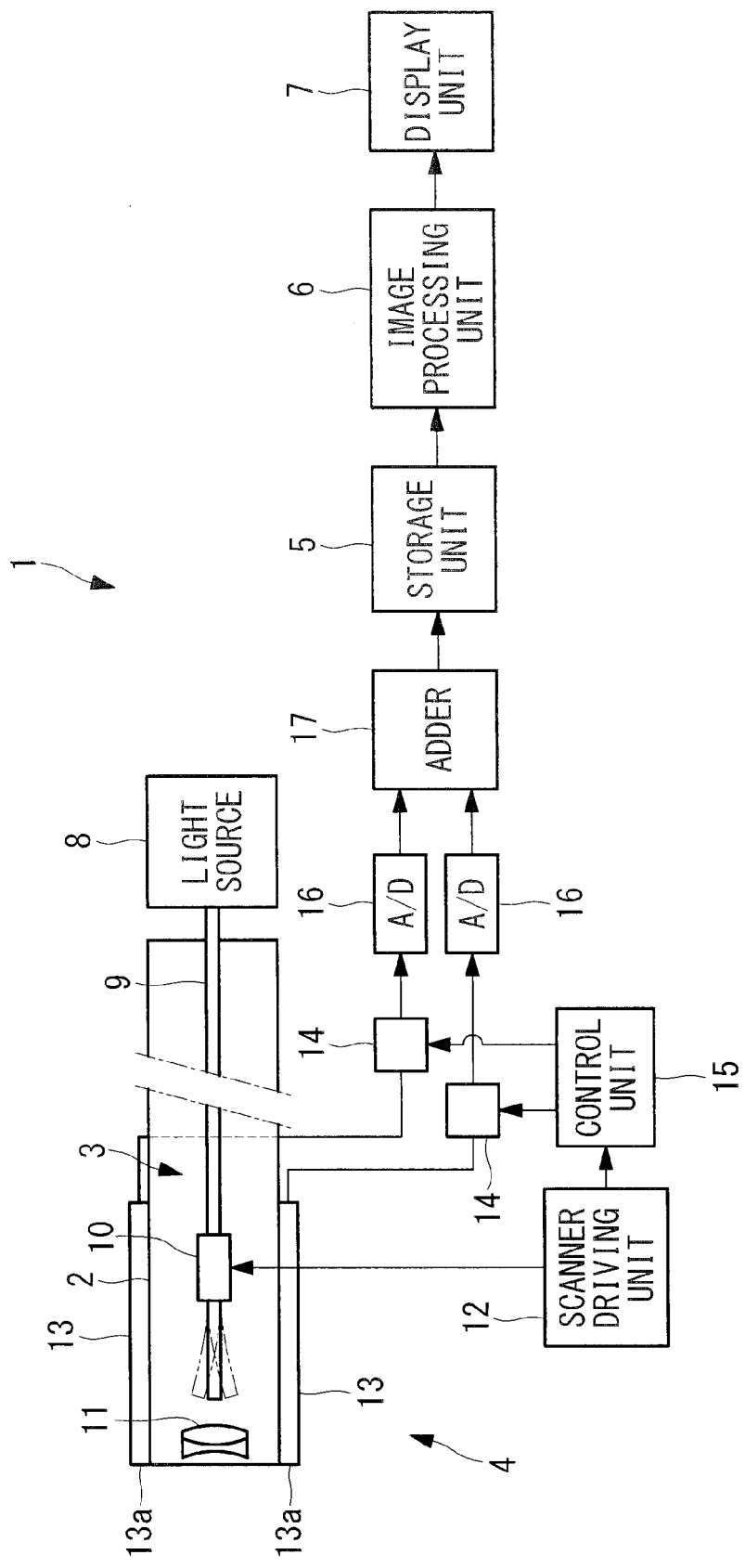
FIG. 1 is a general block diagram of a scanning endoscope according to a first embodiment of the present invention.

As shown in FIG. 1, the scanning endoscope 1 according to the present embodiment includes a thin insertion portion 2, an illumination portion 3 and an optical detection portion 4 which are provided on the insertion portion 2, a storage unit 5 for storing the result of detection by the optical detection portion 4, an image processing unit 6 for generating an image based on information stored in the storage unit 5, and a display unit 7 for displaying the image formed by the image processing unit 6.

The illumination portion 3 includes a light source 8 arranged on the base end side of the insertion portion 2, an optical fiber 9 for guiding illumination light from the light source 8 and emitting the illumination light from a leading edge arranged on a leading edge of the insertion portion 2, and a scanner (optical scanning unit) 10 for moving the leading edge of the optical fiber 9 in the direction crossing the longitudinal axis of the insertion portion 2 to change the direction in which the illumination light is emitted. A reference numeral 11 denotes an illumination lens.

The scanner 10 is an electromagnet or a piezoelectric element and directs the leading edge of the optical fiber 9 to an angle or a direction according to the input voltage.

Figure 2:
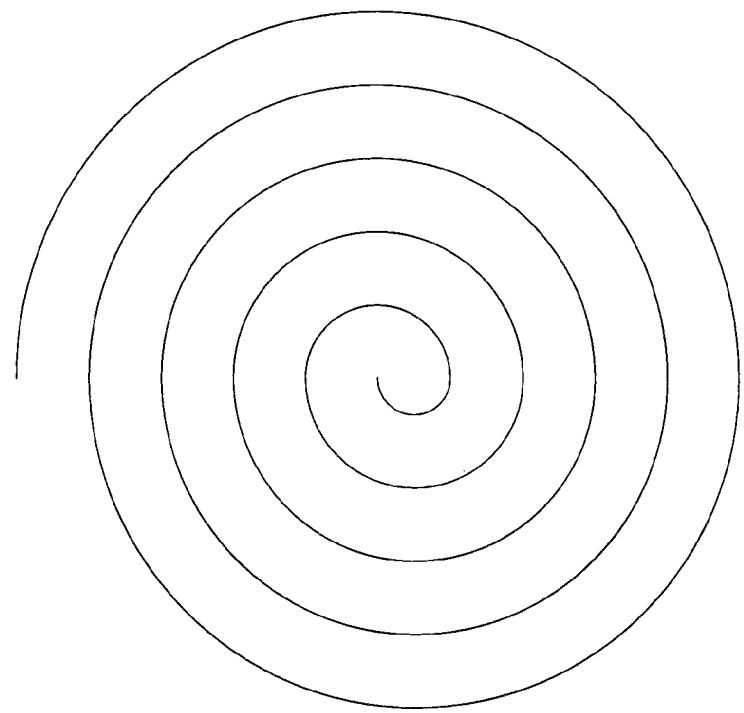
FIG. 2 is an example of a locus of illumination light scanned by the scanning endoscope in FIG. 1.

In the present embodiment, the scanner 10 rotates the leading edge of the optical fiber 9 to emit the illumination light along the spiral locus shown in FIG. 2.

The scanner 10 is connected to a scanner driving unit 12 and moved according to an instruction signal output from the scanner driving unit 12.

The scanner driving unit 12 outputs the instruction signal for rotating the leading edge of the optical fiber 9 around the center axis of the insertion portion 2 while gradually changing a distance of the leading edge of the optical fiber 9 to the center axis to move the leading edge of the optical fiber 9 along the spiral locus.

Figure 3:
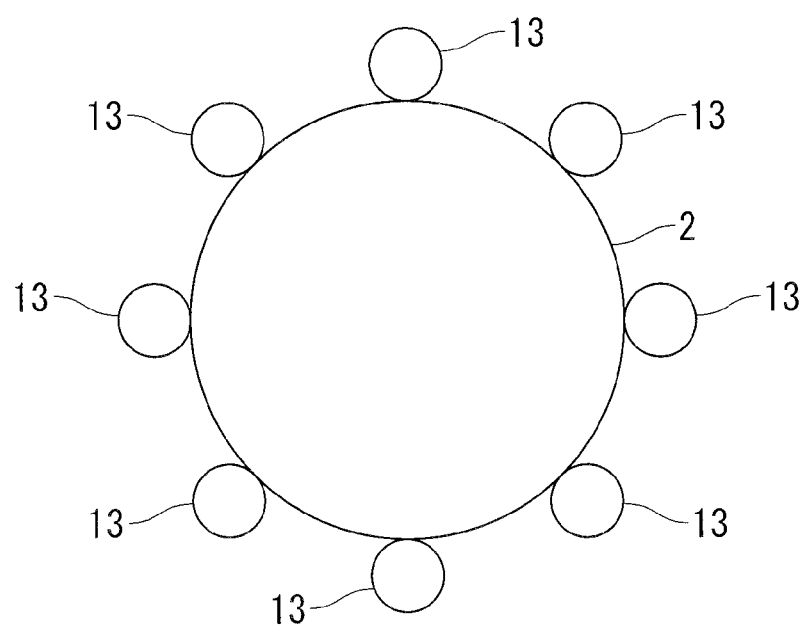
FIG. 3 is a front view showing an example where light receiving portions of the scanning endoscope shown in FIG. 1 are arranged.
Figure 4:
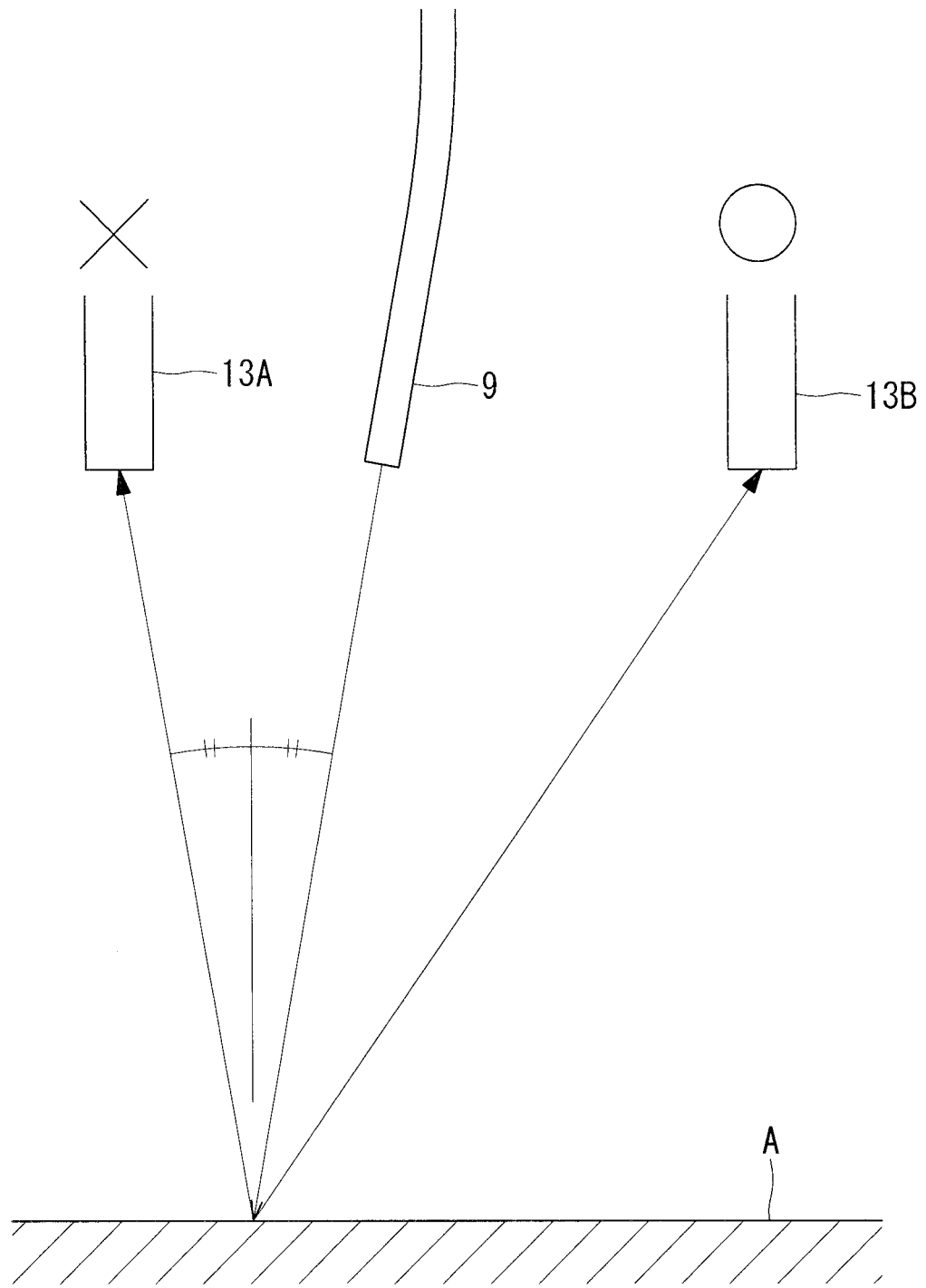
FIG. 4 is a schematic diagram describing how return light is selected by the scanning endoscope in FIG. 1.

As shown in FIG. 3, the optical detection portion 4 includes a plurality of light receiving portions 13 (eight light receiving portions in the example shown in FIG. 3, for example) circumferentially spaced apart around the periphery of the insertion portion 2, photodetectors 14 respectively connected with the light receiving portions 13, and a control unit (return light selection unit) 15 for controlling the operation condition of the photodetectors 14. The light receiving portion 13 is an optical fiber for guiding light, for example, and serves to guide the light received at a leading edge surface 13a of the light receiving portion 13 to the base end side.

The photodetector 14 is a photomultiplier tube (PMT), for example, which is connected with the base end side of the light receiving portion 13 and detects the light received and guided by the light receiving portion 13. The photomultiplier tube outputs a current signal according to the intensity of the detected light. Analog-to-digital (A/D) converters 16 are connected to the photomultiplier tubes and convert current signals according to the intensity of the detected light to digital signals.

A plurality of the A/D converters 16 is connected to an adder 17. The digital signals output from all the A/D converters 16 are added by the adder 17 and output the signals to the storage unit 5 as a single piece of strength information.

The control unit 15 turns on and off the driving power sources of the photodetectors 14 in synchronization with the instruction signal input from the scanner driving unit 12. More specifically, when the leading edge of the optical fiber 9 is disposed in a positional relationship with respect to any of the light receiving portions 13 by the operation of the scanner 10, a relevant light receiving portion 13A receives regular reflection light of the illumination light in an object A, so that the driving power source of the photodetector 14 connected with the light receiving portion 13A is turned off when the leading edge is disposed in such a positional relationship. When the leading edge is disposed in another positional relationship, that is, in the position of a light receiving portion 13B, for example, the driving power source is turned on.

The timing at which the driving power source of each of the photodetectors 14 is turned off is set for each photodetector 14 according to the rotation angle of the leading edge of the optical fiber 9 and a distance from the center axis of the insertion portion 2. Specifically, prior to observation, the object A is illuminated with the illumination light to detect a scanning position where the return light exceeds a predetermined threshold for each photodetector 14. The driving power source of each of the photodetectors 14 is turned on or off according to the detected timing.

The storage unit 5 is connected with the scanner driving unit 12 and the adder 17 and stores information about the scanning positions of the illumination light by the optical fiber 9 according to the instruction signal output from the scanner driving unit 12 in association with information about the intensity of the return light output from the adder 17.

The image processing unit 6 generates a two-dimensional image such that the intensity of the return light stored in association with the scanning position is arranged in the order of the scanning positions according to the information about the scanning positions stored in the storage unit 5.

The working of the thus configured scanning endoscope 1 according to the present embodiment is described below.

The insertion portion 2 is inserted into an object to be inspected and the leading edge of the insertion portion 2 is opposed to the object A to observe the object A using the scanning endoscope 1 according to the present embodiment.

In this state, the light source 8 is operated to illuminate light illuminated by the light source 8 from the leading edge of the insertion portion 2 via the optical fiber 9 and the scanner driving unit 12 is operated to send an instruction signal to the scanner 10, thereby to move the leading edge of the optical fiber 9. Thereby, the illumination light emitted from the leading edge of the optical fiber 9 is scanned along a spiral locus on the object A.

A plurality of the light receiving portions 13 arranged at the leading edge of the insertion portion 2 receives the return light scattered in various directions from the object A and corresponding to each scanning position of the illumination light and the photodetectors 14 connected to the light receiving portions 13 detect the intensity of the return light. The intensity detected by the photodetectors 14 is converted into a digital signal by the A/D converters 16, the digital signal is added by the adder 17, and a single piece of strength information associated with the scanning position is stored in the storage unit 5.

In this case, according to the scanning endoscope 1 of the present embodiment, the driving power sources of the photodetectors 14 are turned off in the scanning position where the intensity of the return light detected by the photodetectors 14 exceeds the predetermined threshold. As a result, there is no pixel extraordinarily high in the strength in the image generated by the image processing unit 6, which provides an advantage that the occurrence of halation can be prevented to allow observation by a clear image.

In the present embodiment, the example in which eight optical fibers are circumferentially spaced apart is cited as the light receiving portions 13, however, two or more light receiving portions 13 may be arranged instead.

The scanner 10 that moves the position of the leading edge of the optical fiber 9 to scan the illumination light is exemplified, however, scanning may be performed by swinging a mirror or using an electro-optic crystal instead.

In the present embodiment, the control unit 15 serving as the return light selection unit turns off the operation of the photodetector 14 on which excessively strong return light is incident to selectively detect only the return light equal to or smaller than the predetermined threshold, however, a light shielding means such as a shutter or a combination thereof may be used instead.

Figure 5:
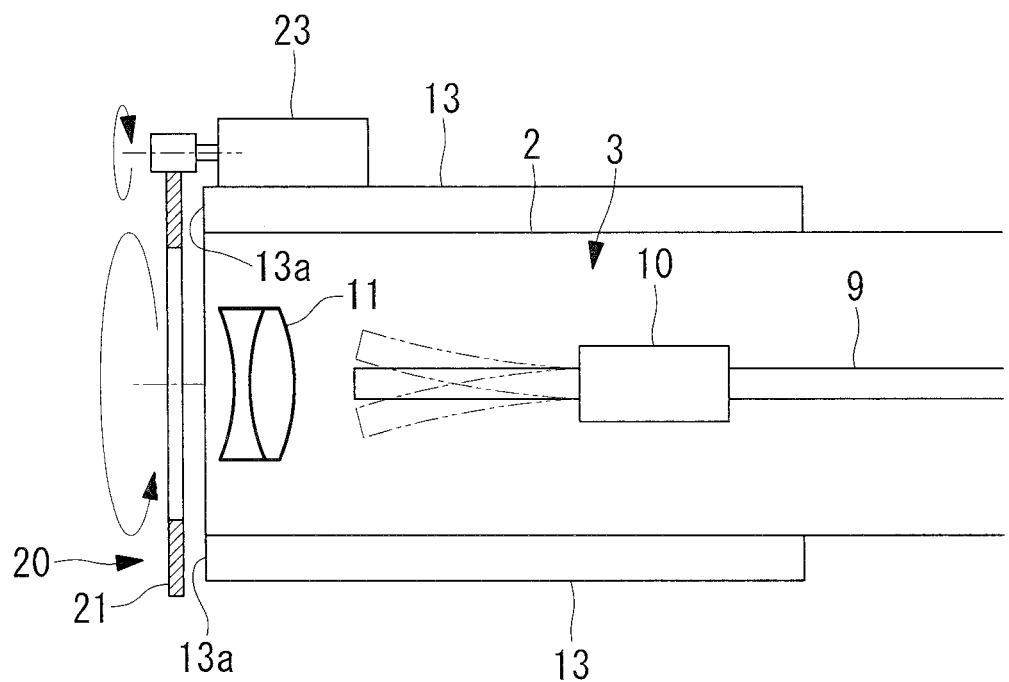
FIG. 5 is a detailed schematic diagram in the vicinity of a leading edge of an insertion portion showing a modified example of a return light selection unit of the scanning endoscope in FIG. 1.
Figure 6:
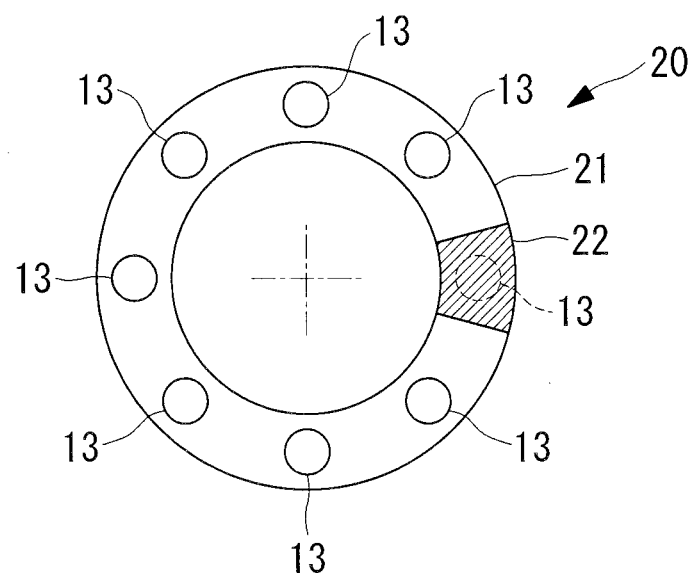
FIG. 6 is a front view showing an example of the return light selection unit in FIG. 5.

As shown in FIG. 5 and FIG. 6, a shutter 20 includes a light shielding unit 22 which is arranged in front of the leading edge surface 13a of the light receiving portion 13 and shields a circumferential part of a toroidal transparent member 21 attached rotatably around a center axis C of the insertion portion 2, and a motor 23 for rotating the transparent member 21. The transparent member 21 is rotated by the operation of the motor 23 to cause the light shielding unit 22 provided in the transparent member 21 to allow precluding the return light from being incident on the light receiving portion 13 arranged in opposition.

The shielding unit 22 may selectively shield each of the light receiving portions 13 or a plurality of the light receiving portions 13 at the same time.

Shielding the leading edge surface 13a of the light receiving portion 13 by the light shielding unit 22 at the timing at which the regular reflection light high in intensity is incident thereon allows preventing halation from occurring on the generated image.

In this case, a common photodetector 14 may be arranged on a plurality of the light receiving portions 13. This allows the number of the photodetectors 14 to be reduced and addition processing to be reduced in the adder 17.

A toroidal shutter shown in FIG. 6 may be arranged between the light receiving portion 13 and the photodetector 14. Also in this case, the light shielding unit 22 shields from light the light receiving surface of the photodetector 14 at the timing at which the regular reflection light high in intensity is incident thereon to allow preventing halation from occurring on the generated image.

Figure 7:
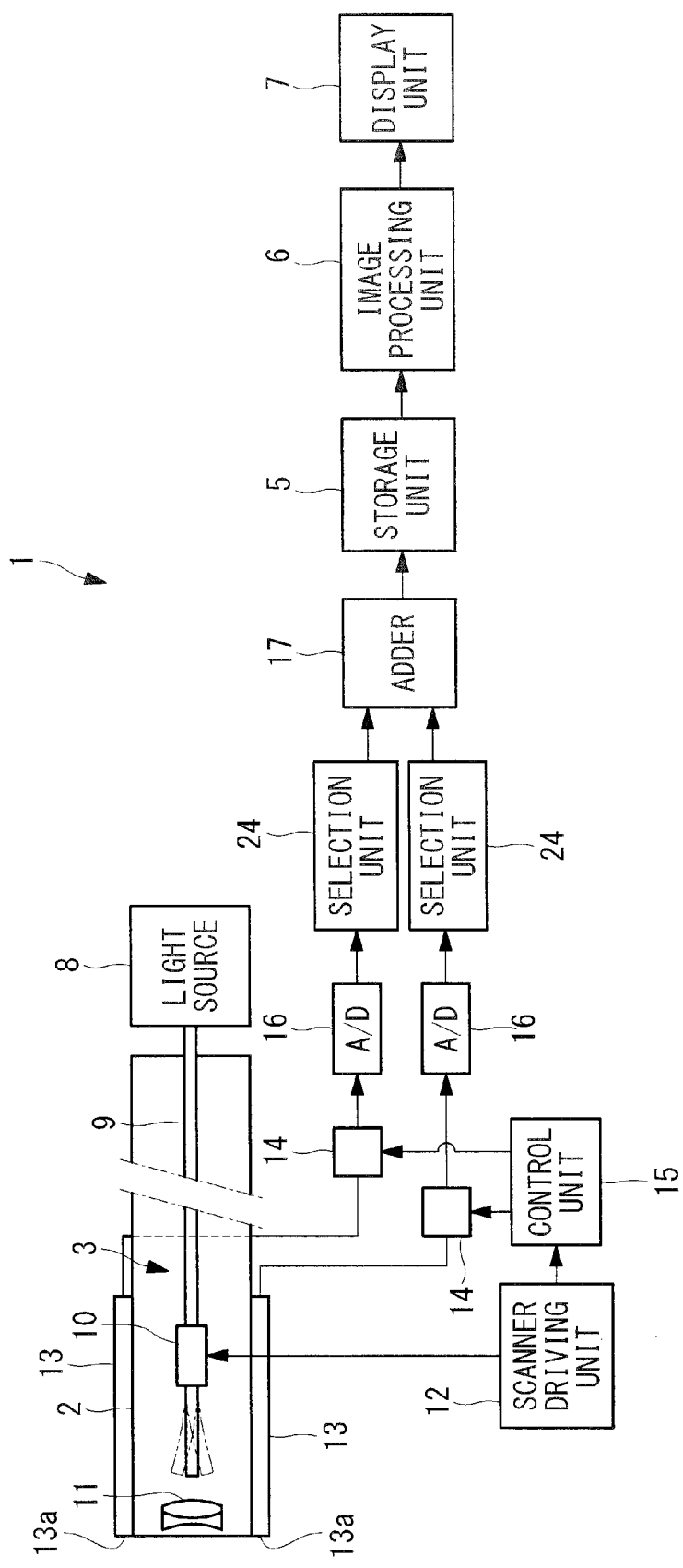
FIG. 7 is a general block diagram of another modified example of the scanning endoscope in FIG. 1.

As a modified example of the return light selection unit shown in FIG. 7, operation may be performed by signal processing in which the control unit 15 controls the image processing unit 6, only a signal whose intensity is equal to or smaller than a threshold is selected by a selection unit 24 after the signal showing the intensity of the return light output from the photodetector is converted into a digital signal by the A/D converter, and the selected intensity is added by the adder 17.

Alternatively, operation may be performed by such a signal processing that only a signal with intensity exceeding a threshold is selected as a halation-related signal by the selection unit 24 and the output of the halation-related signal is made zero or is not added in the adder 17.

Other than those, the selection unit 24 may select the return light excluding the return light whose intensity is the highest by excluding a signal in which the intensity of the return light output from the photodetector is the highest instead of selecting the return light by the threshold. That is, only the signal in which the intensity of the return light output from the photodetector is the highest is selected by the selection unit 24 as a halation-related signal and operation may be performed by signal processing in which the output of the halation-related signal is made zero or is not added in the adder 17. Thereby, glare including halation and overexposure can be dissolved or reduced.

Similarly, the selection unit 24 may select the return light excluding the return light whose intensity is the highest and the lowest by excluding a signal in which the intensity of the return light output from the photodetector is the highest and the lowest instead of selecting the return light by the threshold. That is, the selection unit 24 may select the signal in which the intensity of the return light output from the photodetector is the highest and the lowest as a halation-related signal and operation may be performed by signal processing in which the output of the halation-related signal is made zero or is not added in the adder 17. Thereby, glare and disorder in image due to unexpected noise can be reduced.

Thus, an unnecessary signal is removed according to purposes from among the return light output from the photodetector by suppressing halation or reducing noise to allow generating a desired image.

If there is a plurality of signals representing intensities of the return lights selected by the selection unit 24, an average calculation unit (not shown) for calculating an average value of the intensities may be provided and the storage unit 5 may store the average value of the intensities of the return lights associated with the scanning position of the illumination lights by the scanner 10. Thereby, the image processing unit 6 arranges the return lights stored in the storage unit 5 in association with the scanning positions in the order of the scanning positions to allow a two-dimensional image to be generated based on the average value of intensities of the return lights.

According to the present invention, even if the scanning locus of the optical fiber is not spiral, like a Lissajous shape, for example, can be applied to any scene where the illumination light emitted from the leading edge of the insertion portion of the endoscope changes every moment at various angles. According to the above modified example, even if an object itself shows various shapes or changes in shape like a living body, the modified example has the advantage that a clear image can always be generated without reflecting halation or noise in an image according to the intensity of the return light output from the photodetector.

From the above-described embodiment, the following inventions are derived.

According to an aspect of the present invention, a scanning endoscope includes an optical scanning unit in which an angle at which illumination light is emitted from a leading edge of an insertion portion is changed to scan the emitted illumination light on an object, a plurality of light receiving portions which is circumferentially spaced apart at the leading edge of the insertion portion and receives return light returning from the object as a result of the optical scanning unit scanning the illumination light, a light detection unit that detects an intensity of the return light received by the light receiving portion, a return light selection unit that selects the return light whose intensity, which is detected by the light detection unit, is equal to or smaller than a predetermined threshold, and a storage unit that stores the intensity of the return light selected by the return light selection unit in association with a position where the optical scanning unit scans the illumination light.

According to the aspect, the leading edge of the insertion portion is opposed to an object and the optical scanning unit is operated to cause illumination light to scan the object while an angle at which the illumination light is emitted from the leading edge of the insertion portion is being changed. The return light returned from the object due to the emission of the illumination light, such as reflection light on the surface of the object, fluorescence emitted by exciting a fluorescent material in the object, and scattered light in which light is scattered in the object and returned, for example, is received by the light receiving portion arranged in the leading edge of the insertion portion and the intensity thereof is detected by the light detection unit. The return light whose intensity is equal to or smaller than the predetermined threshold among the return lights is selected by the return light selection unit and the intensity of the selected return light is stored in the storage unit in association with the position where the optical scanning unit scans.

The intensity associated with the scanning position is arranged for each scanning position to allow the image of the object to be generated. In this case, the intensity of the return light which is equal to or smaller than the predetermined threshold is stored in the storage unit and selected, so that a pixel extremely high in intensity is not included in the generated image, which prevents halation from occurring to allow a clear image to be generated.

In the above aspect, the return light selection unit may change the return light to be selected in synchronization with the operation of the optical scanning unit.

Thereby, the operation of the optical scanning unit enables efficiently removing the return light whose luminance is high such as regular reflection light generated when the emitting angle of the illumination light and the light receiving portion are arranged in a predetermined positional relationship.

In the above aspect, the optical scanning unit may rotate the leading edge of an optical fiber emitting the illumination light along a spiral locus and the return light selection unit may change the return light to be selected according to the angle at which the optical scanning unit rotates the optical fiber.

Thereby, the leading edge of the optical fiber is rotated along the spiral locus by the operation of the optical scanning unit to scan the illumination light emitted from the leading edge of the optical fiber on the object along the spiral locus.

In this case, the direction in which the illumination light is emitted from the leading edge of the optical fiber and the light receiving portion are arranged in a predetermined positional relationship according to the angle at which the optical scanning unit rotates the optical fiber, so that the return light selected by the return light selection unit is changed according to the rotation angle of the optical fiber to allow effectively remove high-intensity return light such as periodically generated regular reflection light from information stored for generating images.

In the above aspect, the return light selection unit may be a light shielding unit that selectively limits the incidence of the return light on each of the light receiving portions.

Thereby, the return light selection unit composed of the light shielding unit shields from light the light receiving portion at the timing at which high-intensity return light is incident on the light receiving portion to allow preventing the high-intensity return light from being incident on the light detection unit, enabling preventing the occurrence of inconvenience such as deterioration of the light detection unit.

In the above aspect, the light detection unit may be provided for each of the light receiving portions and the return light selection unit may be a light shielding unit that selectively limits the incidence of the return light on each of the light detection units.

Thereby, the return light selection unit composed of the light shielding unit shields from light the light detection unit corresponding to the light receiving portion at the timing at which high-intensity return light is incident on the light receiving portion to allow preventing the high-intensity return light from being incident on the light detection unit, enabling preventing the occurrence of inconvenience such as deterioration of the light detection unit.

In the above aspect, the light detection unit may be provided for each of the light receiving portions and the return light selection unit may switch the operation state of each of the light detection units.

Thereby, the return light selection unit stops the operation of the light detection unit corresponding to the light receiving portion at the timing at which high-intensity return light is incident on the light receiving portion to allow preventing the high-intensity return light from being detected by the light detection unit.

In the above aspect, the return light selection unit may compare the intensity of the return light detected by the light detection unit with the threshold to select return light whose intensity is equal to or smaller than the threshold.

Thereby, the return light whose intensity is equal to or smaller than the threshold among the return lights detected by the light detection unit is selected and stored, so that a pixel extremely high in intensity is not included in the generated image, which prevents halation from occurring to allow a clear image to be generated.

According to another aspect of the present invention, a scanning endoscope includes an optical scanning unit in which an angle at which illumination light is emitted from a leading edge of an insertion portion is changed to scan the emitted illumination light on an object, a plurality of light receiving portions which is circumferentially spaced apart at the leading edge of the insertion portion and receives return light returning from the object as a result of the optical scanning unit scanning the illumination light, a light detection unit that detects the intensity of the return light received by the light receiving portion, a return light selection unit that excludes the return light whose intensity is highest, the return light being detected by the light detection unit, to select return light excluding the return light whose intensity is the highest, and a storage unit that stores the intensity of the return light selected by the return light selection unit in association with a position where the optical scanning unit scans the illumination light.

According to the aspect, the leading edge of the insertion portion is opposed to the object and the optical scanning unit is operated to cause illumination light to scan the object while an angle at which the illumination light is emitted from the leading edge of the insertion portion is being changed. The return light returning from the object due to the emission of the illumination light, such as reflection light on the surface of the object, fluorescence emitted by exciting a fluorescent material in the object, and scattered light in which light is scattered in the object and returned, for example, is received by the light receiving portion arranged in the leading edge of the insertion portion and the intensity thereof is detected by the light detection unit. The return light whose intensity is the highest among the return lights is excluded, the return light excluding the return light whose intensity is the highest is selected by the return light selection unit, and the intensity of the selected return light is stored in the storage unit in association with the position where the optical scanning unit scans.

Thereby, the intensity associated with the scanning position is arranged for each scanning position to allow the image of the object to be generated. In this case, the return light whose intensity is the highest, stored in the storage unit, is excluded, so that a pixel extremely high in intensity is not included in the generated image, which prevents halation from occurring to allow a clear image to be generated.

In the above aspect, the return light selection unit excludes the return light whose intensity is the lowest, the return light being detected by the light detection unit, to select return light excluding the return light whose intensity is the highest and the lowest.

Thereby, pixels extremely high and low in intensity are not included to prevent halation from occurring as well as to reduce noise, allowing a clear image to be generated.

In the above aspect, it is preferable that an average calculation unit that calculates an average value of intensity of the return light selected by the return light selection unit is provided and the storage unit stores the average value of intensities of the return light calculated by the average calculation unit in association with the position where the optical scanning unit scans the illumination light.

Thereby, the intensity associated with the scanning position is arranged for each scanning position to allow preventing halation from occurring and generating the image of an object based on the average value of the return light whose noise is reduced.

REFERENCE SIGNS LIST

A Object
1 Scanning endoscope
2 Insertion portion
5 Storage unit
6 Image processing unit
10 Scanner (optical scanning unit)
13, 13A, and 13B Light receiving portion
14 Photodetector (light detection unit)
15 Control unit (return light selection unit)
22 Light shielding unit (light shielding means)
24 Selection unit (return light selection unit)

The invention claimed is:

1. A scanning endoscope comprising:
an optical scanning unit in which an angle at which illumination light is emitted from a leading edge of an insertion portion is changed to scan the emitted illumination light on an object;
a plurality of light receiving portions which is circumferentially spaced apart at the leading edge of the insertion portion and receives return light returning from the object as a result of the optical scanning unit scanning the illumination light;
a light detection unit that detects an intensity of the return light received by the light receiving portion;
a return light selection unit that selects the return light whose intensity, which is detected by the light detection unit, is equal to or smaller than a predetermined threshold; and
a storage unit that stores the intensity of the return light selected by the return light selection unit in association with a position where the optical scanning unit scans the illumination light.

2. The scanning endoscope according to claim 1, wherein the return light selection unit changes the return light to be selected in synchronization with an operation of the optical scanning unit.

3. The scanning endoscope according to claim 2, wherein the optical scanning unit rotates the leading edge of an optical fiber emitting the illumination light along a spiral or a Lissajous locus and the return light selection unit changes the return light to be selected according to an angle at which the optical scanning unit rotates the optical fiber.

4. The scanning endoscope according to claim 1, wherein the return light selection unit is a light shielding unit that selectively limits the incidence of the return light on each of the light receiving portions.

5. The scanning endoscope according to claim 1, wherein the light detection unit is provided for each of the light receiving portions and the return light selection unit is a light shielding unit that selectively limits the incidence of the return light on each of the light detection units.

6. The scanning endoscope according to claim 1, wherein the light detection unit is provided for each of the light receiving portions and the return light selection unit switches an operation state of each of the light detection units.

7. The scanning endoscope according to claim 1, wherein the return light selection unit compares the intensity of the return light detected by the light detection unit with the threshold to select return light whose intensity is equal to or smaller than the threshold.

8. A scanning endoscope comprising:
   an optical scanning unit in which an angle at which illumination light is emitted from a leading edge of an insertion portion is changed to scan the emitted illumination light on an object;
   a plurality of light receiving portions which is circumferentially spaced apart at the leading edge of the insertion portion and receives return light returning from the object as a result of the optical scanning unit scanning the illumination light;
   a light detection unit that detects an intensity of the return light received by the light receiving portion;
   a return light selection unit that excludes return light whose intensity exceeds a predetermined threshold, the return light being detected by the light detection unit, to select return light excluding the return light whose intensity exceeds the predetermined threshold; and
   a storage unit that stores the intensity of the return light selected by the return light selection unit in association with a position where the optical scanning unit scans the illumination light.

9. The scanning endoscope according to claim 8, wherein the return light selection unit excludes the return light whose intensity is highest, the return light being detected by the light detection unit, to select return light excluding the return light whose intensity is the highest.

10. The scanning endoscope according to claim 9, wherein the return light selection unit excludes the return light whose intensity is lowest, the return light being detected by the light detection unit, to select return light excluding the return light whose intensity is the highest and the lowest.

11. The scanning endoscope according to claim 8, further comprising an average calculation unit that calculates an average value of intensity of the return light selected by the return light selection unit, wherein the storage unit stores the average value of intensities of the return light calculated by the average calculation unit in association with the position where the optical scanning unit scans the illumination light.

* * * * *